United States Patent [19]
Bradley et al.

[11] Patent Number: 5,374,275
[45] Date of Patent: Dec. 20, 1994

[54] SURGICAL SUTURING DEVICE AND METHOD OF USE

[75] Inventors: James G. Bradley, Santa Barbara; Michael Fisher, El Dorado Hills, both of Calif.

[73] Assignee: Synvasive Technology, Inc., Rancho Cordova, Calif.

[21] Appl. No.: 37,572

[22] Filed: Mar. 25, 1993

[51] Int. Cl.$^5$ ............................................. A61B 17/04
[52] U.S. Cl. .................................. 606/144; 606/139; 606/148
[58] Field of Search ......................... 606/139, 144, 148; 294/93, 94, 95, 97; 112/163, 169

[56] References Cited

U.S. PATENT DOCUMENTS

| | | |
|---|---|---|
| 659,422 | 10/1900 | Schidler . |
| 2,108,206 | 2/1938 | Meeker . |
| 4,493,323 | 1/1985 | Albright et al. . |
| 4,553,543 | 11/1985 | Armarasinghe . |
| 5,100,421 | 3/1992 | Christoudias . |
| 5,304,184 | 4/1994 | Hathaway et al. ................. 606/144 |

FOREIGN PATENT DOCUMENTS 1174036  8/1985  U.S.S.R. .

Primary Examiner—Stephen C. Pellegrino
Assistant Examiner—Gary Jackson
Attorney, Agent, or Firm—Raymond B. Cranfill

[57] ABSTRACT

A surgical device for closing an incision created by a trocar or similar surgical device is disclosed. The surgical device comprises a support member within which are disposed a first and second needle positioning means. Each of these means carries a suture needle in retrorse configuration relative to the distal end of the support member. The needles can be retracted or deployed relative to the support member in a plurality of desired positions. In operation, the needles are deployed at a desired distance from the edge of the incision. The surgeon then pulls the device out of the body of the patient, thereby capturing and pulling the needles through first the peritoneum followed by the fascia. Needle capture means are provided which retain and remove the needles after the peritoneum and fascia are sutured, leaving the loose ends of the suture thread which can then be tied off below skin level to close the incision.

25 Claims, 4 Drawing Sheets

SURGICAL SUTURING DEVICE AND METHOD OF USE

FIELD OF THE INVENTION

The invention relates generally to surgical suturing devices, and more particularly to intra-abdominal suturing devices designed for closing puncture wounds created by surgical trocars and similar puncturing devices.

BACKGROUND OF THE INVENTION

Minimally invasive surgery is a revolutionary new technique that replaces standard invasive surgical operations requiring large incisions with operations utilizing very small incisions. In this technique, access to the surgical field is made through very small incisions (generally 5-18 mm in diameter) via a surgical trocar. Tubes are then inserted through the incision to permit the further introduction of miniaturized instruments that can be manipulated by a surgeon while viewing the surgical field on a television monitor. This technology affords the patient considerably less pain and disfigurement, and a much faster recovery. The rapid return of the patient to productive activity further reduces the ultimate cost of the surgery.

Although trocars are widely used to puncture the abdominal wall as a first step in minimally invasive surgical techniques, such use creates several serious clinical problems. The very small size of the incision and the somewhat awkward access to the interior facies of the tissues surrounding the incision make closure of the incision problematic and time consuming. For example, one method requires the introduction of a pre-threaded suture needle approximately 3-5 mm from the edge of the original trocar incision. The surgeon views the needle via a laparoscope as it pierces the abdominal wall. The surgeon then grasps the ligature in the pre-threaded needle with a forceps, eventually secures it, passes it to an empty needle that has been introduced on the opposite side of the surgical defect, and withdraws the empty needle up through the other side of the incision, through the abdominal wall, and ties off the suture. The knot is generally tied under the skin to avoid residual external scarring.

Because the surgeon cannot directly visualize the exact position of the needle until after it has passed completely through the abdominal wall, several insertions may be required in order to place the needle at an ideal and proper distance from the trocar incision. The distance from the needle location to the original incision is critical in that the needle must be far enough from the trocar incision to secure an optimal amount of abdominal wall tissue. If the needle distance from the incision is too small, an insufficient amount of tissue will be secured with a consequent risk of inadequate closure of the surgical defect. This may result in subsequent herniation of the omentum or bowel. However, if needle distance from the point of the original trocar incision is too great, incision closure will result in excessive tissue being grasped, and the patient will be left with an unsightly "knot" of tissue.

Aside from attendant awkwardness and the problems resulting therefrom, this method is time-consuming, serendipitous, and produces only marginal closure integrity. Further, this method affords a very significant risk to the patient in that the more or less blind nature of needle insertion, placement and removal may result in laceration of additional blood vessels, thereby exacerbating blood loss and increasing operation time until the damaged blood vessels can be secured and controlled.

Another common technique for closing a trocar incision comprises the reapproximation of the fascia and subcutaneous fat by means of a small needle introduced through the trocar skin incision from outside the body at the termination of the procedure. The difficulty with this technique is that the edges of the fascia are not visualized, with the result that tying the ligature may or may not effectively reapproximate the edges of the fascia. Certainly the peritoneal defect is not effectively closed by this approach because the suture is not placed deeply enough. Further, the blood vessels that are prone to be injured (and therefore bleed) by insertion of the trocars tend to be located immediately external to the peritoneal layer. Because the suture ligature is more or less superficial, suturing of the incision is generally inadequate to ligate these deeper blood vessels.

Often times, closure of the trocar incision is nothing more than skin deep, the deeper layers of the fascia remaining free. Failure to make complete closure of the incision entails a significant risk of delayed bleeding (occurring after the abdomen is deflated and the tamponading effect of the inflated abdomen ceases), or the possibility of herniation of either omentum or bowel into the subcutaneous opening.

Occasionally, the peritoneal defect may be approximated by a traditional, curved-needle suture ligature that is placed from within the abdominal cavity under direct vision. The knot is then tied either by means of an intra-corporeal or extra-corporeal knot-tying technique. This approach is rarely used because it is cumbersome, requires a high level of skill, and is still not optimal as it ensures only that the peritoneum is closed, closure of the more exterior fascia being purely speculative.

In view of the foregoing there is a clear need for a suturing device and method of incision closure that is accurate and reliable, and that does not require an excessive amount of time to complete.

There is also a need for a suturing device that positions the needle in a desired location without excessive risk of injury to blood-carrying vessels.

There also exists a need for a surgical device and method that can be utilized by a surgeons having various skill levels.

A further need is for a suturing device that allows the surgeon to place the suturing needles precisely at a desired distance from and at a desired angular orientation relative to the original trocar incision.

SUMMARY OF THE INVENTION

It is a general object of the invention therefore to provide an apparatus and method for rapid and accurate closure of surgical incision caused by the use of a trocar-type puncture device.

It is another object of the invention to provide a method of minimizing excess bleeding caused by inadvertent laceration of blood vessels during closure of a trocar incision.

Another object of the invention is to provide a suturing device that accurately places suture needles in a plurality of radial positions as desired by the surgeon.

It is yet another object of the invention to provide a suturing device that places suture needles in a plurality of distances from the edge of the incision being closed.

Yet another object of the invention is to provide a device that allows a surgeon to close both the peritoneum and fascia surrounding an incision in a single manipulation.

Still another object of the invention is to provide a suturing device and method for closure of trocar incisions that can be successfully used by surgeons having a variety of skill levels.

These objects are met by the invention, which provides a suture device comprising an elongate support member supporting a first and second needle positioning means. Each needle positioning means supports a suture needle in retrorse configuration relative to the distal end of the support member. The needle support means are capable of retracting the suture needles flush to or within the body of the elongate support member for ease of insertion of the device into the body. Once inserted, the needle support means are used to deploy the suture needles to a desired position relative to the edges of the trocar incision. Once the needles are deployed, the entire instrument is pulled toward the surgeon, resulting in the piercing of the peritoneum and fascia by the suture needles, thereby suturing the incision. Since sutures can be tied off underneath the skin level, thus, residual scarring is reduced.

According to yet another embodiment of the invention, the suturing device is provided with a needle capture means. The needle capture means is deployed after puncture of the deeper layers of the abdominal wall, i.e., the peritoneum and fascia, is complete. The needle capture means is generally comprised of a plunger connected to an elastic needle capture or retrieving band that is extended laterally of the wall of the elongate support member. The needles are then brought in contact with the needle capture means wherein they become imbedded. Movement of the needle capture means away from the needle support means accomplishes removal of the needles from the needle support means, leaving the free suture ends for the surgeon to manipulate as desired.

The invention is clearly advantageous over existing devices and methods for closing trocar incisions. In particular, the device allows suturing needles to be placed with precision and ensures that the peritoneum and fascia will be captured and closed during the suturing process. The invention effectively and significantly reduces the threat of post-operative herniation and bleeding.

The device and method of the invention are also advantageous in that they are far less awkward and cumbersome to use than existing techniques. In particular, the threat of damage to collateral blood vessels and tissue is greatly reduced, along with operation time involved in closing the incision. Also, the device is easily utilized by surgeons having a variety of skill levels.

These and other objects of the invention will become more fully apparent when the following detailed description of the invention is read in conjunction with the accompanying drawings.

DETAILED DESCRIPTION OF THE INVENTION

Figure 1:
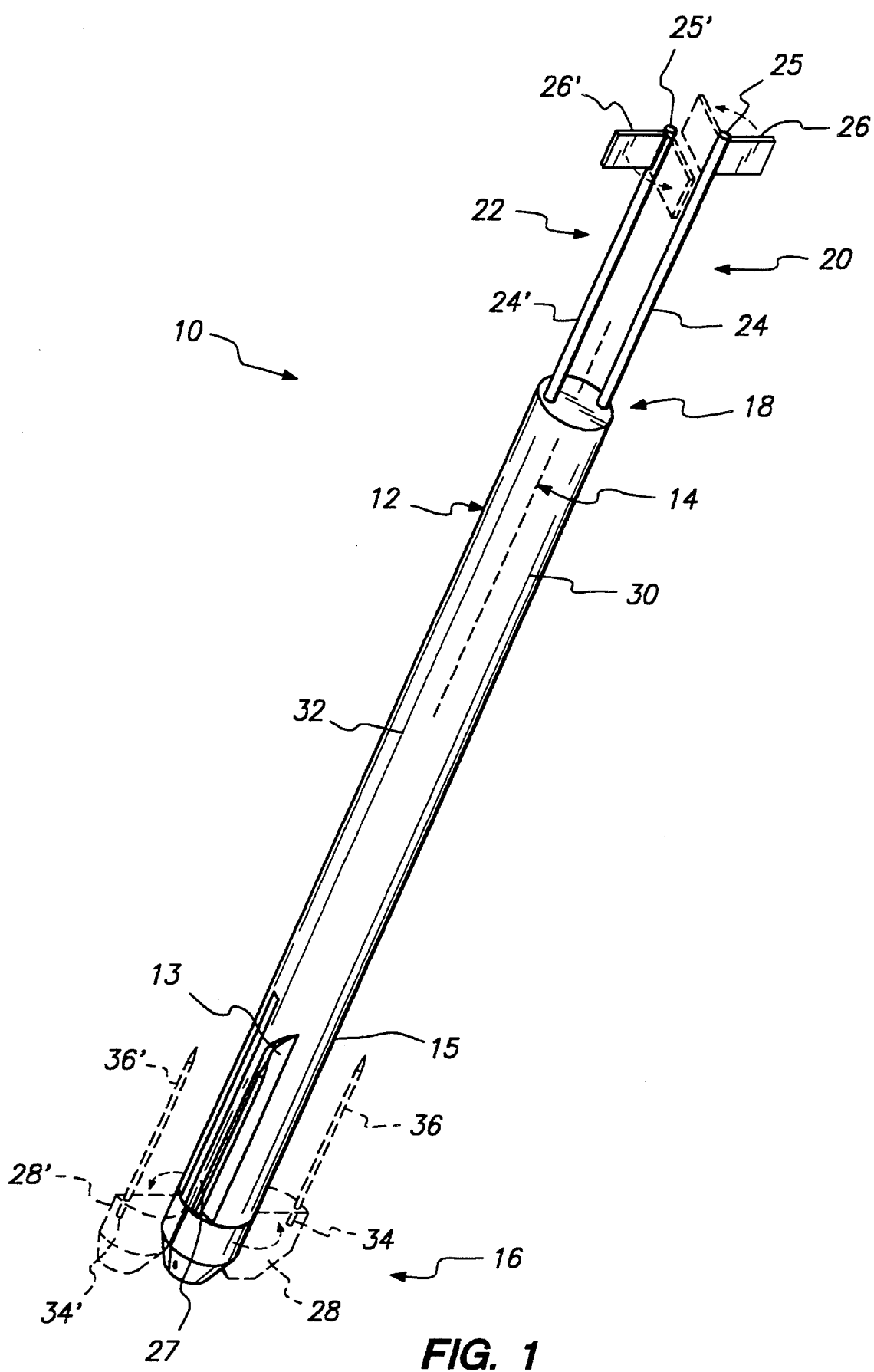
FIG. 1 is an elevated view in perspective of a first embodiment of the surgical device of the invention with phantom lines depicting the needle positioning means in a deployed configuration.

Referring now to the figures, the surgical device 10 of the invention will be described. Surgical device 10 is comprised of an elongate support member 12 having a central axis 14, a distal end 16, a proximal end 18, a first needle retention depression 13 and a second needle retention depression 15. Elongate support member 12 is further provided with a first needle positioning means 20 and a second needle positioning means 22, Each of needle positioning means 20 and 22 comprises a support shaft 24 having a proximal end 25 and a distal end 27, a grasp 26 and a needle support or platform 28. Grasp 26 is fixed to the proximal end 25 of support shaft 24, whereas needle platform 28 is fixed to the distal end 27 of support shaft 24. Each needle platform 28 is provided with a needle retention channel 34 for the releasable receipt of a suture needle 36.

First needle positioning means 20 is slidably and rotatably disposed within said elongate support member 12 along a first lateral axis 30 that is substantially parallel to but spaced apart from the central axis 14 of the elongate support member. Similarly, second needle positioning means 22 is slidably and rotatably disposed within the elongate support member 12 along a second lateral axis 32, that is positioned substantially opposite the first lateral axis 30 relative to and at substantially the same distance from the central axis 14. It will be appreciated that because the needle positioning means 20 and 22 are both axially slidable and rotatable, the suture needle 36 of each needle positioning means can be both extended with respect to the distal end of the elongate support member, as well as radially arrayed with respect to the central axis of the elongate support member.

Figure 2:
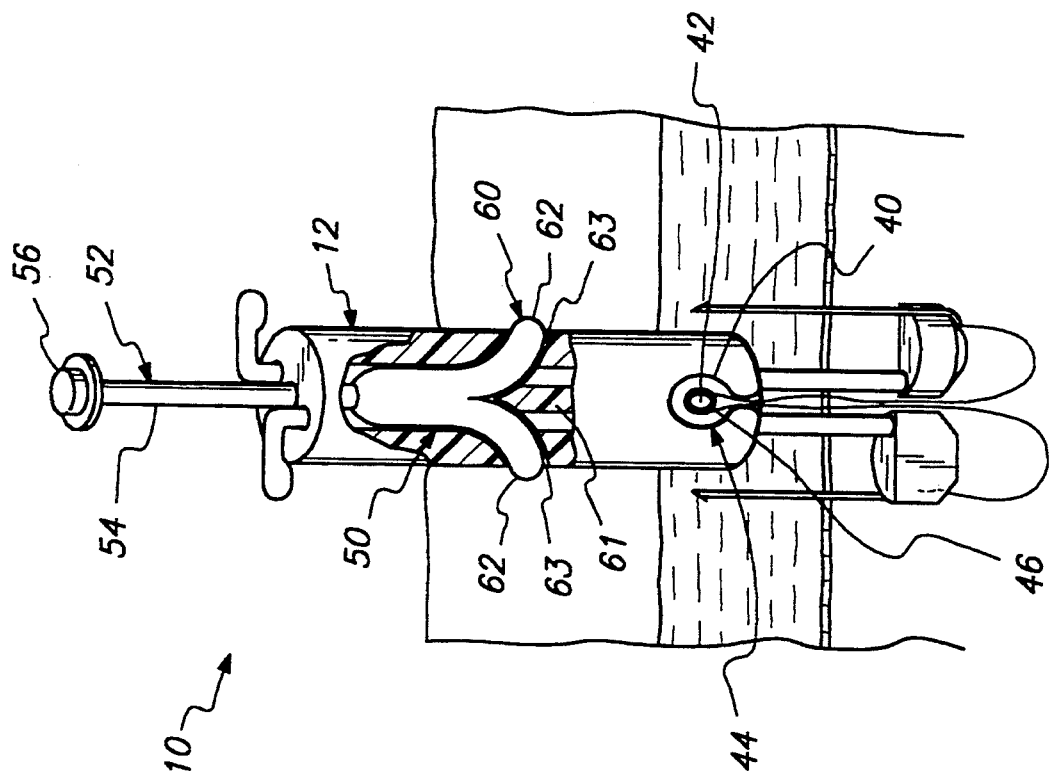
FIG. 2 is a view in perspective with partial cut away of a second embodiment of the device of the invention wherein the needles of the device have been deployed and suturing of the peritoneum has begun.

According to another aspect of the invention as shown generally in FIG. 2, a second embodiment of surgical device 10 is provided. As will become apparent from inspection of the figures, this second embodiment is similar in most respects to the embodiment just described, particularly with regard to the structure, placement and operation of needle positioning means 20 and 22. However, the second embodiment is further provided with a suture retention means 40 and a needle capture means 50.

Suture retention means 40 comprises a suture catch 42 formed from a knob-like projection or similar protuberance. Suture catch 42 is positioned on an exterior surface of the elongate support member 12 more or less proximate to the distal end of the support member. The suture catch may be purely surficial in placement, or more preferably is positioned within a suture depression or well 44. The suture catch may be further provided with a circumferential channel 46 for receipt of the suture thread. As can be seen in FIG. 2, a central portion of a suture thread is captured on suture catch 42 within channel 46. Each end of the suture thread is then extended outward from suture well 44, and separately threaded in either of the suture needles 36. This configuration is preferred and helps to ensure that the suture does not disengage and become lost during operation of surgical device 10.

The second embodiment is further provided with a needle capture means 50 comprising a plunger 52 having a plunger shaft 54 and a plunger handle 56. The needle capture means is further provided with a retrieving band or needle capture 60. Needle capture 60 is fixedly attached to the end of plunger 52 opposite plunger handle 56. Needle capture 60 is divided into two lobes or segments 62. These segments are ultimately responsible for the capture, retention and removal of suture needles 36 prior to closure of the incision.

Figures 6, 7:
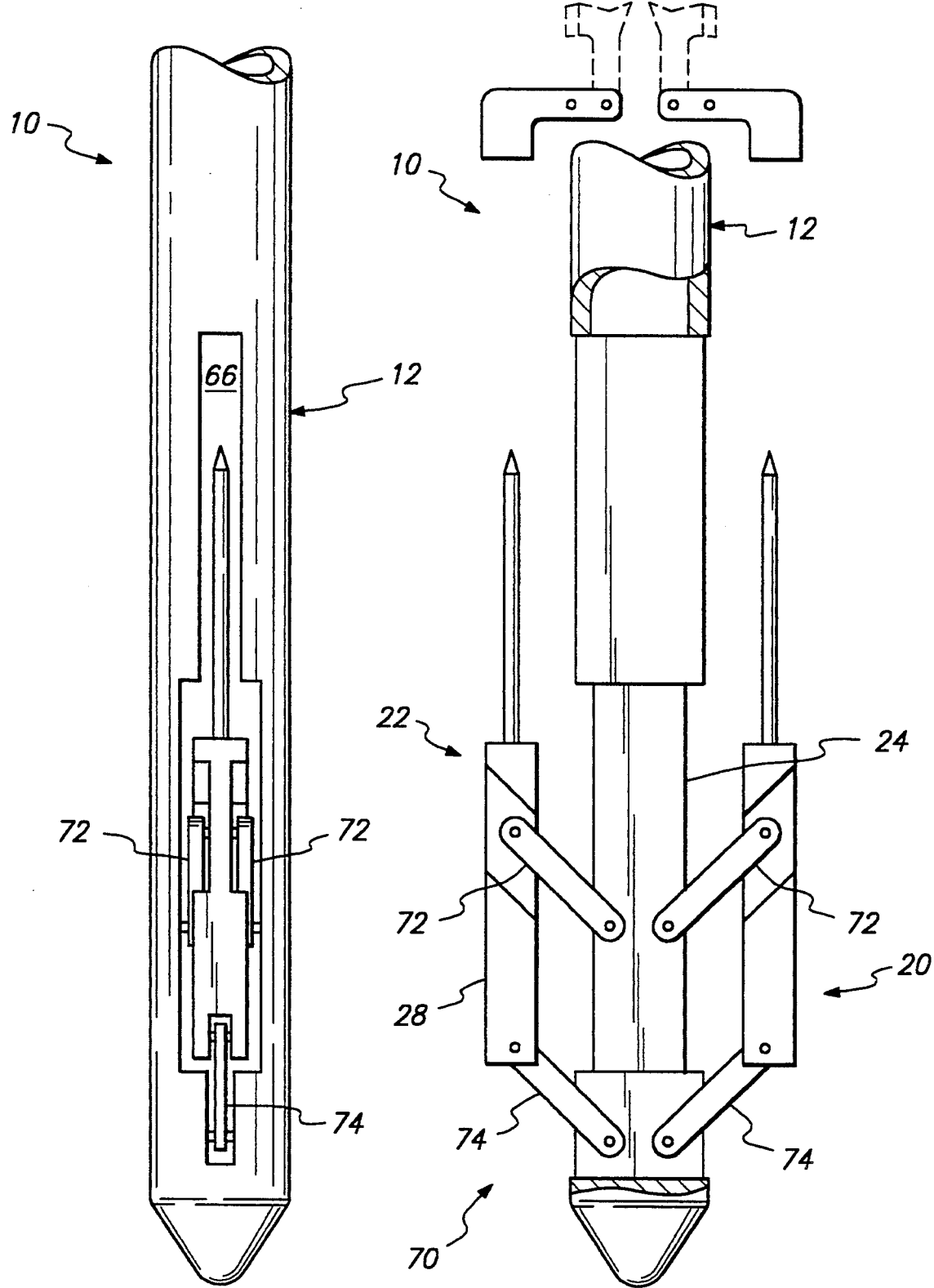
FIG. 6 is a side view of a third embodiment of the surgical device of the invention wherein the needles are in a retracted position.
FIG. 7 is a front view of a third embodiment of the surgical device of the invention wherein the needles are in a deployed position.

It will be appreciated that other configurations of needle positioning means are possible other than those just described. For example, an embodiment employing pivot means is shown if FIGS. 6 and 7. In this embodiment, the elongate support member 12 is provided with retention channels 66 within which needle positioning means can be retracted for insertion of the device of for when the device is not in use. Needle positioning means 20 and 22 are further characterized in having the needle platform 28 connected to the support shaft 24 of the needle positioning means by a pivot means 70. The pivot means comprise a pair of bridge members 72 that are substantially parallel to one another as well as to leg member 74, each of which extend between and movably interconnect the support shaft to the needle platform as shown in FIG. 7. It will be understood from inspection of the figure that needle positioning means 20 and 22 can be retracted within retention channels 66, by sliding the support shaft toward the distal end of the elongate support member. Alternatively, the needle positioning means can be deployed by pulling the support shaft toward the proximal end of the elongate support member. Although a pivot means has been described, it will be understood by one skilled in the art that a rack and pinion means (not illustrated) could be substituted wherein the support shaft could be provided with a pinion for displacing a rack connected to a needle platform. In this way the needle positioning means could be retracted or deployed by a desired incremental distance.

Fabrication of each component of the medical device 10 as described above is made from standard known materials. In fact, every component except the suture needles 36 can be fabricated from polymer plastic so long as the plastic is biocompatible. Although polymer plastic is one possible choice, the grasp 26 and support shaft 24 of the needle support means can also be fabricated from a biocompatible metal, such as surgical steel. Nevertheless, it is preferred to fabricate the needle platform 28 from a polymer plastic, in as much as the needle retention channel 34 is more easily configured using plastic than metal. With regard to needle capture 60, an elastomeric material such as rubber, or some rubberized plastic polymer, is preferred.

The operation of suture device 10 will now be described with reference to the second embodiment of the invention as illustrated in FIGS. 2-6. In operation, surgical device 10 is first threaded with a suture of desired composition, diameter and length by securing a central portion of the suture about the suture catch 42 and then extending the ends of the suture out of suture well 44 and through each of the suture needles 36. After threading, needle positioning means 20 and 22 are placed in a retracted position by axially rotating the support shaft 24 of each until the suture needles 24 are flush against the needle depression channels 13 and 15. Further retraction of the suture needles 36 into a suitable position can be accomplished by pulling the needle positioning means toward the proximal end of the elongate support member until the tip of each needle is proximate to the edge of the needle retention depression. In this configuration, surgical device 10 is ready for insertion through a trocar incision into a body cavity.

After the device is inserted to an appropriate depth as determined by the surgeon viewing the site through a laparoscope, generally to a level below the interior face of the peritoneum, the needle positioning means can then be adjusted to deploy the suture needles. The exact position of the needles will depend on the size and location of the trocar incision. In any case, the needles should be deployed at a sufficient distance from the central axis 14 of the elongate support member 12 in order to ensure that the peritoneum and fascia will be captured during the suturing process.

Figure 3:
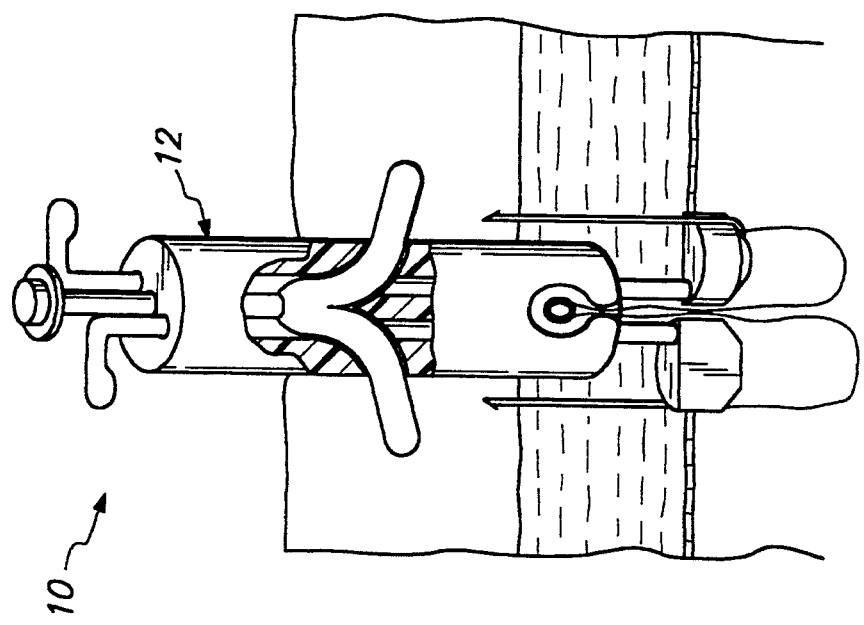
FIG. 3 is a view in perspective with partial cut away of the embodiment shown in FIG. 2 wherein suturing has proceeded to include capture of the fascia and wherein the needle capture means has been deployed.
Figure 4:
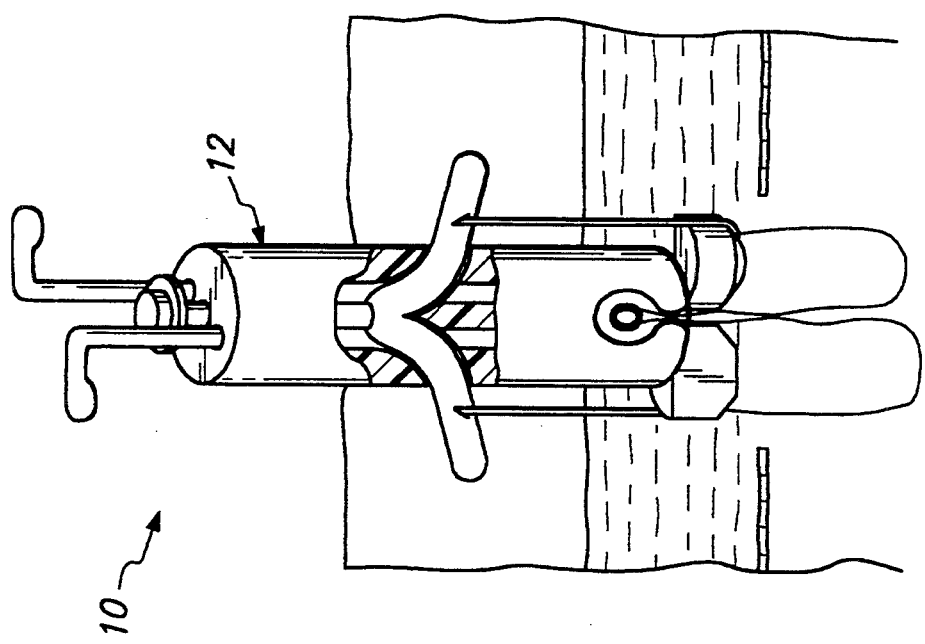
FIG. 4 is a view in perspective with partial cut away of the embodiment shown in FIG. 3 wherein the needle capture means have engaged the suturing needles.

Once the suture needles 36 are deployed at an appropriate distance, the surgical device 10 is slowly but steadily retracted from the body cavity by the surgeon, thereby piercing the peritoneum, as shown in FIG. 2. As the device is pulled further toward the surgeon and out of the body cavity, the suturing needles engage the fascia along the edges of the incision. Once the fascia has been engaged and the skin layer approached, the surgeon deploys the needle capture means 50 by pushing down on the plunger 52. This action forces the tip of the needle capture against the obdurator 61, causing each of the segments 62 to be forced laterally relative to the movement of the plunger, ultimate causing each segment 62 to emerge from the body of the elongate support member through apertures 63, as shown in FIG. 3. Needle capture is accomplished by slidably retracting the needle positioning means toward the surgeon and the proximal end of the elongate support member, as shown in FIG. 4, in order to imbed the piercing end of the needles 36 in needle capture 60.

Figure 5:
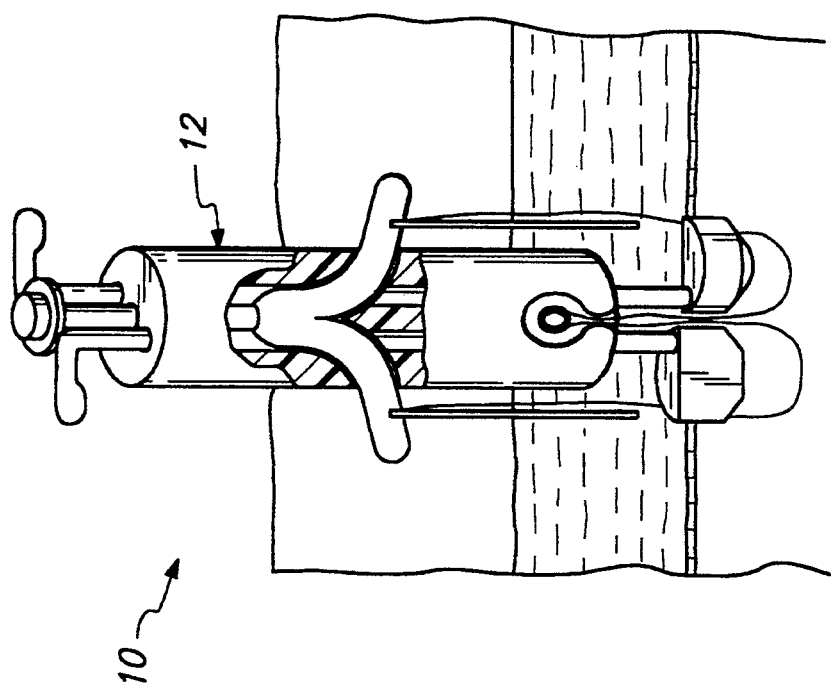
FIG. 5 is a view in perspective with partial cut away of the embodiment shown in FIG. 4 wherein the needles have been removed from the needle positioning means by the needle capture means.

Once the surgeon ascertains that the needles 36 are securely imbedded in the needle capture means, the capture means is retracted within the body of the elongate support member by the surgeon pulling the plunger toward himself. This process results in the removal of the needles from the needle platforms 28, and allows the surgeon to withdraw the surgical device 10 from the body cavity, as shown in FIG. 5. After removal, the surgeon is presented with the free ends of the suture, which he can then tie off subcutaneously to close the incision. The remaining cutaneous surface wound is then closed conventionally by any well known method designed to minimize scarring.

Alternative to the method just described, a suturing device according to the invention but lacking a needle capture means, such as the first embodiment described above, can also be used. In such a case, the method of incision closure is the same as that just described, except the suturing device is further withdrawn by the surgeon in order that the needles pierce and emerge above the outer skin layers of the patient. The needles are then removed manually. Following needle removal, the suture threads are retrieved subdermally by any means well known in the art, and the free ends thereby brought into and out of the incision opening. The sutrure ends are then tied off as described above, thereby capturing and sealing the peritoneum and fascial layers adjacent to the incision. The remaining cutaneous surface wound is then closed conventionally by any well known method designed to minimize scarring.

It will now be appreciated that the invention is advantageous over the prior art in several important respects. First, the invention provides a reliable means of fully closing a trocar incision, including both the peritoneum and fascia, such that the risk of post-operative herniation is greatly reduced.

The invention also provides a surgical device and method that permit precise placement of suturing needles so that the risk of unintended damage to blood-carrying vessels is greatly reduced.

The invention is further advantageous in that use of the invention does not require highly specialized surgical skills, affording even beginning surgeons the ability to close a trocar incision quickly and reliably.

The invention is also advantageous over the prior art in that it provides a means for much more rapid closure of trocar incisions than currently exists, thereby reducing operation time and cost.

Although the surgical device and method of the invention have been described with respect to specific embodiments, it will be appreciated that various modifications of and changes to the surgical device and method are possible without departing from the invention, the scope of which is defined and set forth in the claims that follow.

I claim:

1. A surgical device for closing an incision with a suture, said device comprising:
   a) an elongate support member having a central axis, a distal end, and a proximal end;
   b) a first needle configured for carrying a first end of the suture;
   c) a first needle positioning means for releasable support of the first needle in retrorse configuration relative to the distal end of said support member, said first needle support means movably disposed within said support member along a first lateral axis substantially parallel to but spaced apart from the central axis of said elongate support member and capable of deploying the first needle at a plurality of distances outward from said support member;
   d) a second needle configured for carrying a second end of the suture; and
   e) a second needle positioning means for releasable support of a second needle in retrorse configuration relative to the distal end of said support member, said second needle support means movably disposed within said support member along a second lateral axis substantially opposite the first lateral axis relative to the central axis and capable of deploying the second needle at a plurality of distances outward from said support member.

2. The surgical device of claim 1 further comprising a suture support means for releasable capture of a portion of the suture extending between the first and second needles, said suture support means positioned near the distal end of said elongate support member.

3. The surgical device of claim 2 wherein said suture support means is positioned within a depression on an exterior surface of said elongate support member.

4. The surgical device of claim 1 wherein each of said first and second needle support means comprises:
   a) a support shaft movably mounted within said elongate support member and further characterized in having a proximal end extending exterior to the proximal end of said elongate support member and a distal end;
   b) a grasp connected to the proximal end of the support shaft; and
   c) a needle platform connected to the distal end of the support shaft and provided with a needle retention channel for releasable receipt of a needle.

5. The surgical device of claim 4 wherein said first and second needle positioning means are further provided with rack and pinion means interconnecting the support shaft and the needle platform, said rack and pinion means for adjustable deployment of said first and second needles.

6. The surgical device of claim 4 wherein said first and second needle positioning means are further provided with pivot means interconnecting the support shaft and the needle platform, said pivot means for adjustable deployment of said first and second needles.

7. A surgical device for closing an incision with a suture, said device comprising:
   a) an elongate support member having a central axis, a distal end, and a proximal end;
   b) a first needle configured for carrying a first end of the suture;
   c) a first needle positioning means for releasable support of the first needle in retrorse configuration relative to the distal end of said support member, said first needle support means having a support shaft movably mounted within said elongate support member along a first lateral axis substantially parallel to but spaced apart from the central axis of said elongate support member and further characterized in having a proximal end extending exterior to the proximal end of said elongate support member and a distal end, a grasp connected to the proximal end of the support shaft, and a needle platform connected to the distal end of the support shaft and provided with a needle retention channel for releasable receipt of a needle, said needle support means capable of deploying the first needle at a plurality of distances outward from said support member;
   d) a second needle configured for carrying a second end of the suture;
   e) a second needle positioning means for releasable support of a second needle in retrorse configuration relative to the distal end of said support member, said second needle support means having a support shaft movably mounted within said elongate support member along a second lateral axis substantially parallel to but opposite the first lateral axis relative to the central axis of said elongate support member and further characterized in having a proximal end extending exterior to the proximal end of said elongate support member and a distal end, a grasp connected to the proximal end of the support shaft, and a needle platform connected to the distal end of the support shaft and provided with a needle retention channel for releasable receipt of a needle, said second needle support means capable of deploying the second needle at a plurality of distances outward from said support member; and f) a suture support means for releasable capture of a portion of the suture extending between the first and second needles, said suture support means positioned within a depression along an exterior distal portion of said elongate support member.

8. A surgical device for closing with a suture an incision created by a trocar or similar instrument, said device comprising:

a) an elongate support member having a central axis, a distal end, and a proximal end;

b) a first needle configured for carrying a first end of the suture;

c) a first needle positioning means for releasable support of the first needle in retrorse configuration relative to the distal end of said support member, said first needle support means movably disposed within said support member along a first lateral axis substantially parallel to but spaced apart from the central axis of said elongate support member and capable of deploying the first needle at a plurality of distances outward from said support member;

d) a second needle configured for carrying a second end of the suture;

e) a second needle positioning means for releasable support of a second needle in retrorse configuration relative to the distal end of said support member, said second needle support means movably disposed within said support member along a second lateral axis substantially opposite the first lateral axis relative to the central axis and capable of deploying the second needle at a plurality of distances outward from said support member; and f) needle capture means for capture and removal of the first and second needles after suturing, said needle capture means movably disposed along the central axis of said elongate support member.

9. The surgical device of claim 8 further comprising a suture support means for releasable capture of a portion of the suture extending between the first and second needles, said suture support means positioned near the distal end of said elongate support member.

10. The surgical device of claim 9 wherein said suture support means is positioned within a depression on an exterior surface of said elongate support member.

11. The surgical device of claim 8 wherein each of said first and second needle support means comprises:

a) a support shaft movably mounted within said elongate support member and further characterized in having a proximal end extending exterior to the proximal end of said elongate support member and a distal end;

b) a grasp connected to the proximal end of the support shaft; and c) a needle platform connected to the distal end of the support shaft and provided with a needle retention channel for releasable receipt of a needle.

12. The surgical device of claim 11 wherein said first and second needle positioning means are further provided with rack and pinion means interconnecting the support shaft and the needle platform, said rack and pinion means for adjustable deployment of said first and second needles.

13. The surgical device of claim 11 wherein said first and second needle positioning means are further provided with pivot means interconnecting the support shaft and needle platform, said pivot means for adjustable deployment of said first and second needles.

14. A surgical device for closing with a suture an incision created by a trocar or similar device, said device comprising:

a) an elongate support member having a central axis, a distal end, and a proximal end;

b) a first needle configured for carrying a first end of the suture;

c) a first needle positioning means for releasable support of the first needle in retrorse configuration relative to the distal end of said support member, said first needle support means having a support shaft movably mounted within said elongate support member along a first lateral axis substantially parallel to but spaced apart from the central axis of said elongate support member and further characterized in having a proximal end extending exterior to the proximal end of said elongate support member and a distal end, a grasp connected to the proximal end of the support shaft, and a needle platform connected to the distal end of the support shaft and provided with a needle retention channel for releasable receipt of a needle, said needle support means capable of deploying the first needle at a plurality of distances outward from said support member;

d) a second needle configured for carrying a second end of the suture;

e) a second needle positioning means for releasable support of a second needle in retrorse configuration relative to the distal end of said support member, said second needle support means having a support shaft movably mounted within said elongate support member along a second lateral axis substantially parallel to but opposite the first lateral axis relative to the central axis of said elongate support member and further characterized in having a proximal end extending exterior to the proximal end of said elongate support member and a distal end, a grasp connected to the proximal end of the support shaft, and a needle platform connected to the distal end of the support shaft and provided with a needle retention channel for releasable receipt of a needle, said second needle support means capable of deploying the second needle at a plurality of distances outward from said support member;

f) a suture support means for releasable capture of a portion of suture extending between the first and second needles, said suture support means positioned within a depression along an exterior distal portion of said elongate support member; and g) needle capture means for capture and removal of the first and second needles after the incision is sutured, said needle capture means movably disposed along the central .axis of said elongate support member.

15. The surgical device of claim 8 wherein said needle capture means comprises:

a) a plunger slidably disposed along the central axis of and extending exterior to the proximal end of said elongate support member; and b) a needle capture.

16. The surgical device of claim 15 wherein said elongate support member is provided with a first aperture and a second aperture, the first aperture positioned near the proximal end of said elongate support member and the second aperture positioned at a point substantially opposite the first aperture relative to the central axis.

17. The surgical device of claim 16 wherein the needle capture has a proximal end connected to the plunger of said needle capture means and a distal end, the distal end divided into a first lobe configured to pass through and extend exterior of the first aperture of said elongate support member and a second lobe configured to pass through and extend exterior of the second aperture of said elongate support member.

18. The surgical device of claim 17 wherein said needle capture is comprised of an elastic material.

19. The surgical device of claim 14 wherein said needle capture means comprises:
   a) a plunger slidably disposed along the central axis of and extending exterior to the proximal end of said elongate support member; and
   b) a needle capture.

20. The surgical device of claim 19 wherein said elongate support member is provided with a first aperture and a second aperture, the first aperture positioned near the proximal end of said elongate support member and the second aperture positioned at a point substantially opposite the first aperture relative to the central axis.

21. The surgical device of claim 20 wherein the needle capture has a proximal end connected to the plunger of said needle capture means and a distal end, the distal end divided into a first lobe configured to pass through and extend exterior of the first aperture of said elongate support member and a second lobe configured to pass through and extend exterior of the second aperture of said elongate support member.

22. The surgical device of claim 21 wherein said needle capture is comprised of an elastic material.

23. A surgical device for closing with a suture an incision created by a trocar or similar device, said device comprising:
   a) an elongate support member having a central axis, a distal end, and a proximal end;
   b) a first needle configured for carrying a first end of the suture;
   c) a first needle positioning means for releasable support of the first needle in retrorse configuration relative to the distal end of said support member, said first needle support means having a support shaft movably mounted within said elongate support member along a first lateral axis substantially parallel to but spaced apart from the central axis of said elongate support member and further characterized in having a proximal end extending exterior to the proximal end of said elongate support member and a distal end, a grasp connected to the proximal end of the support shaft, and a needle platform connected to the distal end of the support shaft and provided with a needle retention channel for releasable receipt of a needle, said needle support means capable of deploying the first needle at a plurality of distances outward from said support member;
   d) a second needle configured for carrying a second end of the suture;
   e) a second needle positioning means for releasable support of a second needle in retrorse configuration relative to the distal end of said support member, said second needle support means having a support shaft movably mounted within said elongate support member along a second lateral axis substantially parallel to but opposite the first lateral axis relative to the central axis of said elongate support member and further characterized in having a proximal end extending exterior to the proximal end of said elongate support member and a distal end, a grasp connected to the proximal end of the support shaft, and a needle platform connected to the distal end of the support shaft and provided with a needle retention channel for releasable receipt of a needle, said second needle support means capable of deploying the second needle at a plurality of distances outward from said support member;
   f) a suture support means for releasable capture of a portion of suture extending between the first and second needles, said suture support means positioned within a depression along an exterior distal portion of said elongate support member; and
   g) needle capture means for capture and removal of the first and second needles after the incision is sutured, said needle capture means comprising a plunger slidably disposed along the central axis of and extending exterior to the proximal end of said elongate support member and an elastic needle capture having a proximal end connected to the plunger and a distal end divided into a first lobe and a second lobe, said lobes configured to pass through and extend exterior of said elongate support member.

24. A method of suturing and closing an incision created by a trocar or similar surgical instrument, said method comprising the steps of:
   a) inserting through the incision to a point below a patient's peritoneum a pair of needles each having a piercing end and each threaded with an end of a desired length of suture, said needles inserted in retrorse configuration relative to the direction of insertion such that the piercing ends of said needles are directed substantially back toward the peritoneum after insertion;
   b) positioning each of said needles at a distance from the incision sufficient to place each needle beneath peritoneal and fascial tissues;
   c) withdrawing said needles in order to pierce and capture with the suture a portion of both the peritoneal and fascial tissues;
   d) removing each of said needles, leaving behind the ends of the suture;
   e) tying off the ends of the suture, thereby closing the incision by bringing together adjacent portions of the peritoneal and fascial tissues.

25. The method of claim 24 wherein said needles are inserted, positioned and withdrawn substantially simultaneously and in controlled relation to each other.

* * * * *